United States Patent [19]

Nagai et al.

[11] Patent Number: 4,508,728

[45] Date of Patent: Apr. 2, 1985

[54] METHOD OF TREATING INFLAMMATORY DISEASES

[76] Inventors: Kineshiro Nagai; Kinuko Nagai, both of No. 4-22-2, Yoyogi, Shibuya-ku, Tokyo, Japan

[21] Appl. No.: 613,230

[22] Filed: May 24, 1984

[51] Int. Cl.$^3$ .............................................. A61K 31/415
[52] U.S. Cl. ..................................................... 514/400
[58] Field of Search ....................................... 424/273 R

[56] References Cited

U.S. PATENT DOCUMENTS 3,995,051 11/1976 Cook et al. .......................... 424/273

FOREIGN PATENT DOCUMENTS 1076123 9/1976 Canada .
1900697 9/1969 Fed. Rep. of Germany .
2109408 9/1972 Fed. Rep. of Germany .
2128138 10/1972 France .
48-4783 2/1973 Japan .

OTHER PUBLICATIONS

Fujii et al., J. of Med. Chem., 14(354), 1971.
Chem. Abst. Tenth Collective Index Chem. Substances–Heptanol–Imidazolidinamine, 1977–1981, 25580 CS.

*Primary Examiner*—Stanley J. Friedman
*Attorney, Agent, or Firm*—McDermott, Will & Emery

[57] ABSTRACT

Homocarnosine having the chemical formula

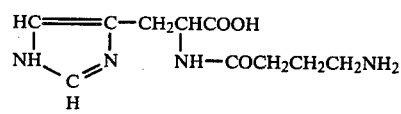

or physiologically acceptable salts thereof are specifically effective as a medicine for treatment of inflammatory diseases.

5 Claims, No Drawings

METHOD OF TREATING INFLAMMATORY DISEASES

BACKGROUND OF THE INVENTION

1. Field of the Invention

This invention relates to a medicine for treatment of inflammatory diseases comprising homocaronosine or physiologically acceptable salts thereof as an effective ingredient and a method of treating inflammatory diseases by use of said medicinal preparation.

2. Brief Description of the Prior Art

An "era" of antiinflammatory medicines, whose main features were their antiedematous, antigranular and antipain effects, began with the discovery of the clinical effects of cortisone in 1949. Today the scope of application of these medicines seems to have reached to its limination.

Therefore, at present there remain many inflammatory diseases for which various medicines based on the former concept of antiinflammation have no beneficial effects at all. For example, these incurable diseases include the decubital ulcer, cornea ulcer, cervical erosion and ulcer of the lower limbs, for which need is felt for an inflammatory therapeutic agent based on a new concept of different from that of antiinflammation.

The so-called natural or spontaneous healing of inflammatory diseases is our ultimate ideal, this desire being shared by those in the medical and dental profession and the laity alike.

However, in the medical tradition, the belief in "Spontaneous healing cannot be promoted" still persists.

BRIEF SUMMARY OF THE INVENTION

One of the objects of the present invention is to provide an effective medicine for treatment of various types of inflammatory diseases containing homocarnosine or physiologically acceptable salts thereof as an effective ingredient.

Another object of the present invention is to present several methods for treating inflammatory diseases by use of this medicine in which homocarnosine is used as a chief ingredient.

The effects of an inflammatory treatment can be assessed by the promotion of granulations that encapsulate insoluble and immovable substances embedded in animals both in experimental pharmacology and pathophysiology. This promotion of granulations is made artificially and this method definitely differs from the present concept of using antiinflammatory medicines to check the inflammatory symptoms.

The inventor discovered the granulation promotive action of homocarnosine through pharmacological experiments he conducted in connection with his study on the action of omega-amino acid on inflammatory phenomenon, homocarnosine being a derivative of omega-amino acid and a physiological substance. This invention is based on this discovery.

DETAILED DESCRIPTION OF THE INVENTION

Homocarnosine, used as an effective ingredient of this newly invented medicine, is a dipeptide, i.e., L-histidinyl-γ-aminobutylic acid, which was discovered in 1961 by Pisano and his associates from the brain extract of cows. This substance exists in the brains at about 0.007% but since the time of its discovery the physiological significance and pharmacological utility of it has remained unexplained.

Homocarnosine is represented by the following chemical formula.

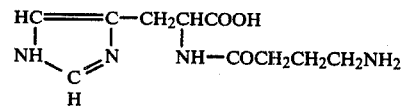

It is a white crystalline powder. m.p. 242°–243° C., $[\alpha]_D^{20} = +23.2°$ A 10% solution of it is colorless and transparent, having slight alkalinity with a correspondingly slight alkaline taste to the tongue. Homocarnosine taken into a vital body will become L-histidine and γ-aminobutylic acid through hydrolysis. L-histidine is an amino acid which is consumed largely from our daily foods as a nutrient and γ-aminobutylic acid is an amino acid which exists in the brain medulla and as a substance to promote the brain metabolism. γ-aminobutylic acid is commercially marketed by the Daiichi Pharmaceuticals Co., under the trade name of Gammaron. The safety of this chemical has been officially confirmed.

Various methods for preparing homocarnosine are known. Homocarnosine can, for example, be synthesized by the method described in The Journal of Biological Chemistry, 236, No. 2: pp. 499–502, 1961. According to this synthesizing method, to a suspension of carbobenzyloxy γ-aminobutylic acid in methylene chloride is added triethylamine. After the resulting solution has been chilled to $-5°$ C., ethyl chloroformate is added and the mixture is kept at this temperature for 10 minutes. To this solution is further added rapidly a solution of L-histidine methyl ester prepared by the addition of triethylamine to a suspension of L-histidine methyl ester dihydrochloride in methylene chloride which has been chilled to 0° C. The resulting mixture is kept overnight at 25° C. It then is washed with water and 1N—NaHCO$_3$, dries over Na$_2$SO$_4$, and concentrated to a syrup. The product is dissolved in methanol and 1N—NaOH is added. After storage for 3 hours at 25° C., the solution is adjusted to pH 5 with addition of dilute H$_2$SO$_4$ and concentrated to dryness under reduced pressure. The residue is extracted with hot ethanol twice, and water is further added to the extract. Following addition of 10% palladium-charcoal, the mixture is hydrogenated in an apparatus equipped with a Caroxite tube for the absorption of CO$_2$. After the hydrogenation, the solution is filtered and concentrated under reduced pressure. The residual syrup is dissolved in water and adjusted to pH 3 with dilute H$_2$SO$_4$. Upon slow addition of ethanol, the dipeptide sulfate separates as granular crystals. The product is filtered and recrystallized from water-ethanol by the same procedure. Homocarnosine sulfate is obtained, m.p. 240° C. (decomposition point). After Dowex 50 is charged into a column and treated with 1N—HCl, the column is washed with water until the wash water proves to be neutral in the presence of thymol blue. A 10% solution of homocarnosine sulfate is passed through the column and the column is washed with water to remove SO$_4''$ until the wash water proves to be neutral in the presence of thymol blue. Homocarnosine is subsequently eluted with 1N—NH$_4$OH. The homocarnosine crystals are obtained after concentration of the solution, addition of ethanol and allowing the solution to stand in a cool room.

The medicines of the present invention also include medicines derived from physiologically acceptable salts of homocarnosine. As the salts of homocarnosine, salts based on carboxyl radicals and addition salts with physiologically acceptable acids based on amino radicals may be mentioned. Salts based on both carboxylic acid and amino radical may also be mentioned. Salts based on carboxyl radical include metallic salts such as sodium, potassium, calcium, magnesium, zinc and aluminum salts, ammonium salts and substituted ammonium salts such as trialkylamine salts, e.g. triethylamine salt. Those based on amino radical include salts with inorganic or organic acids such as hydrochloric, sulfuric, phosphoric, acetic, propionic, lactic, tartaric, citric, succinic, maleic, benzenesulfonic and toluenesulfonic acids. These salts can be prepared by the well-known method, i.e. by the reaction of homocarnosine in its free form with the selected acid or base in stoichiometrical amount.

In the following, experimental examples are cited to demonstrate the effectiveness of homocarnosine as a promoter of healing action for inflammatory diseases.

EXPERIMENTAL EXAMPLE 1

The promotive action of granulation by homocarnosine was examined by a routine formalin filter paper method (FFP method) and the quantitative analysis of hydroxyprolin. For experimental purposes, use was made of groups of 5 or 6 six-week old Wister strain male rats weighing around 170 g each. The hair was sheared from the backs of these animals using clippers and under ether anesthesia they were given an incision of about 1 cm by a shap surgical knife along the dorsal median line. A piece of filter paper (No. 26 product by Toyo Filter Paper Co.) was cut into circles having a diameter of 6.7 mm which were immersed in a 7% formalin solution. In each rat, these filter paper circles, 4 altogether, were inserted underneath the skin of the right and left scapular areas and under the skin about 4 cm to the rear or these areas, two circles on the right side and two on the left side. A dose of penicillin was given to prevent the possibility of infective suppuration subcutaneously and the incised portion was sutured by use of clips. On the second day after the insertion of formalin immersed filter paper, the sutures were removed and on the seventh day they were put to death under ether anesthesia by cutting the carotid vessels, from which the mass of granulations that had been formed by formalin immersed filter paper was taken out. After the entire granular mass containing filter paper was measured for wet weight, the mass from the left scapular area was used for the quantitative analysis of hydroxyprolin. Homocarnosine was prepared in an isotonic solution and was injected into the animals either subcutaneously or peritoneally once daily for seven days after the suture. When an oral administration was needed, it was made in a 15% solution and was poured into the esophagus. The mass of granulations freed from the filter paper was defatted by ethanol-ether and after being rendered in the gelatin state by an autoclave it was added with concentrated hydrochloric acid and was hydrolyzed overnight at a temperature of 105° to 110° C. After it was thickened and dried at 105° to 110° C., the product was added with 0.02N hydrochloric acid and its hydroxyprolin was quantified by a Hitachi-835 amino acid automatic analyzer in an effort to estimate the amount of collagen that had been synthesized.

TABLE 1

| | Effect of Homocarnosine on Granulation (FFP-method) | |
|---|---|---|
| Homocarnosine* | Wet weight (% of control) | Hydroxyproline (% of control) |
| — | 100 (20) | 100 (9) |
| 3 | 96.1 ± 5.6 (18) | 97.8 ± 10.1 (7) |
| 10 | 121.3 ± 5.7$^a$ (20) | 127.6 ± 14.5 (9) |
| 30 | 126.6 ± 7.3$^b$ (19) | 123.9 ± 8.0 (8) |
| 50 | 133.7 ± 7.2 (20) | |
| 70 | 131.7 ± 7.8 (24) | |
| 90 | 135.6 ± 7.2 (20) | |

*Homocarnosine mg/kg i.p.
$^a$p < 0.01
$^b$p < 0.025
( ) Number of granuloma

EXPERIMENTAL EXAMPLE 2

The healing effect of surgical wounds by homocarnosine was assessed in the following manner. Six-week old Wister strain male rats weighing around 170 g each were used. The rats which had their backs denuded over an extensive area by clippers were given an incision of about 4 cm by a sharp surgical knife along the dorsal medial line under ether anesthesia. A dosage of penicillin was administered to prevent the possibility of infective suppuration and the incision was uniformly sutured with silk threads at 3 spots. Homocarnosine was made into isotonic solution which was subcutaneously injected every day into 8 places on both sides of the incision equally for 7 days. Physiologic saline was employed as a control. The threads were removed 4 days after the formation of the incisions and the experimental animals were put to death on the 7th day under ether anesthesia, and 3 pieces of dosal skin, 3 cm in length and 1 cm in width each, were surgically cut off in such manner that the incision line lay at the middle of the piece. One side of each piece of skin was fixed and the other was pulled and the force required to separate the skin at the point the incision had been made was taken to indicate the tensile strength.

TABLE 2

| | Effect of Homocarnosine on the Wound Healing | | |
|---|---|---|---|
| Homocarnosine* | Tensile Strength X + S.E. | No. of skins | % of control |
| — | 454.4 + 29.9 | 17 | 100 |
| 0.06 | 436.8 + 27.6 | 18 | 96.1 |
| 0.6 | 493.3 + 27.5 | 15 | 108.6 |
| 6.0 | 539.6 + 41.5$^a$ | 18 | 118.8 |

*mg/rat i.d.
$^a$p < 0.01

EXPERIMENTAL RESULTS

Table 1 above gives the results of a granulation formation test by FFP-method in which homocarnosine in the amounts of 10, 30, 50, 70 and 90 mg/kg (i.p.) is effective in promoting granulation formation. The quantitative test of hydroxyprolin also indicates that its amount increased in proportion to an increase in the wet weight of granulations. Table 2 gives the effect of homocarnosine on the surgical wounds (ulcers). The efficacy is indicated by the tensile strength of wounds on the 7th day for which homocarnosine was subcutaneously injected into the experimental rats in the amounts of 0.6 and 6.0 mg/rat.

Inflammations of internal organs are named according to the organ concerned and its pathological condition, but fundamentally the cause of the diseases is due to an inflammation of the connective tissues distributed in these organs. The beneficial effect of homocarnosine is non-specific to any given organ and when it is prepared in an adequate concentration and homocarnosine can reach the diseased spot, the healing process of an inflammation will be initiated. Therefore, homocarnosine can be expected to be effective for such diseases as cornea ulcer, conjunctivitis (ophthalmological field), wounds of all sorts (surgical field), dental extraction wounds, aphtha ulcer, angulus infectiosus (dental field), allergic rhinitis, tonsillitis, inflammation of respiratory tract (otorhinolaryngological field), burn, herpes zoster, decubital ulcer, eczema, allergic dermatitis (dermatological field), stomach ulcer, ulcer of duodenum, ulcers of small and large intestines and rectum (digestive field), archosyrinx, hemorrhoid and ulcer of anus (proctological field), cervical erosion, vaginal ulcer, ulcer of the outer genitalia and herpes (gynecological field) and the atheroma ulcer (circulatory field), etc.

When homocarnosine is administered either orally or non-orally depending upon the cases presented, it is equally effective. For instance, it can assume the form of injection solution, powder, granule, tablet, capsule, enteric-coated tablet or capsule, ointment, paste, suppository, clyster, inhalant or troche. It can be administered either singly or conjointly with other medicin or medicines when necessary. The dosage naturally depends largely on the method of administration and the form of homocarnosine preparation is decided by the symptoms of the patient.

The following list gives the typical forms of homocarnosine preparation dosages and methods of administration.

| Form of Preparation | Dosage and administration |
| --- | --- |
| Injection solution | 0.5% homocarnosine solution is used at diseased spots in the amount of 0.1–1.0 ml at one time. |
| Suppository | A suppository containing 20 mg homocarnosine is inserted into diseased spots at one time. |
| Ointment | An ointment of 1% homocarnosine is used at diseased spot at one time. |

Since there are only rough standards and, as stated above, homocarnosine is a very safe chemical compound, the dosage can be increased or decreased freely depending on the symptoms of the patient.

As homocarnosine is readily soluble in water, there is no difficulty in preparing aqueous isotonic solutions of 0.3%, 0.5% and 1.0% under aseptic conditions. The solution thus prepared is put into ampoules under a current of an inert gas and is injected using an ordinary syringe. Alternatively, it is possible to make use of freeze-dried homocarnosine placed in ampoules or vials under aseptic processing and to use it for injectional purposes by making 0.3%, 0.5% or 1.0% isotonic solution just before the injection. Homocarnosine, either in the form of powder, granule, tablet or capsule for oral administration is prepared according to the known method by using binding agents such as syrup, gum arabic, gelatin, sorbit, tragacanth gum or polyvinylpyrrolidone; excipients, such as lactose, corn starch, calcium phosphate, sorbit or glycine; lubricants such as magnesium stearate, talc, polyethyleneglycol, hydroxypropylmethylcellulose or silica; disintegrant such as potato starch; wetting agent such as sodium lauryl sulfate etc. The tablet products may be coated by the use of well known methods in the art. The ointment is produced according to a known procedure by mixing fine powder of homocarnosine in an amount resulting in the desired concentration in the finished ointment with an ointment base, such as bleached beeswax, whale wax, anhydrous lanoline, white petrolatum, higher alcohols, macrogols or Plasti Base (hydrocarbon gel ointment base manufactured by Taisho Pharmaceutical Co., Ltd.), hydrophilic ointment, water absorbing ointment or mixtures thereof. If necessary, oils such as sesame oil, peanut oil and olive oil, resin materials, glycerine, propyleneglycol, surfactant, germicide, fungicide, antioxidant etc., are further added and the mixture thus obtained is kneaded to produce homocarnosine ointment of uniform quality. The homocarnosine suppository is made in almost the same manner as the ointment. For instance, the suppository is prepared by adding antiseptics and homocarnosine into a melted suppository base, mixing thoroughly, casting the mixture into a mold and removing it from the mold when it has solidified.

In the following, there are given several preparations in which homocarnosine is used as a main effective ingredient.

PREPARATION EXAMPLE 1 (INJECTION SOLUTION)

Under aseptic conditions, synthesized homocarnosine was prepared in aqueous isotonic solutions of 0.3%, 0.5% and 1.0% respectively, which were put into the ampoules for the purpose of an injection.

PREPARATION EXAMPLE 2 (GRANULE)

According to the following prescription, granule was prepared.

| Prescription | |
| --- | --- |
| Homocarnosine | 0.2 g |
| Lactose | 0.34 g |
| Cornstarch | 0.45 g |
| Hydroxypropylmethylcellulose | 0.01 g |
| Granule | 1.00 g |

PREPARATION EXAMPLE 3 (OINTMENT)

According to the following prescription, 1% ointment was prepared using a hydrocarbon gel ointment base and synthesized homocarnosine.

| Prescription | |
| --- | --- |
| Homocarnosine | 1.0 g |
| Hydrocarbon gel ointment base | 99.0 g |
| Ointment | 100.0 g |

PREPARATION EXAMPLE 4 (SUPPOSITORY)

According to the following prescription, a suppository was prepared using Hosco S-55 (suppository base manufactured by Maruishi Pharmaceutical Co., Ltd.) as a suppository base and synthesized homocarnosine.

| Prescription | |
|---|---|
| Homocarnosine | 0.02 g |
| p-Oxyethylbenzoate | 0.00085 g |
| Hosco S-55 base | 1.5 g |

(per suppository)

In preparing this suppository, homocarnosine and p-oxyethylbenzoate were sieved using a 200-mesh sieve and were added little by little into the Hosco S-55 base melted at 50° C. so as to obtain a uniform mixture. The mixture was poured into a mold at 38° C. and after cooling at room temperature, it was frozen in a freezer. The product thus obtained was removed from the mold and wrapped up in paraffin paper.

In the following section, reports are made of our clinical tests on dental extraction wounds, aftha stomatitis, angulus infectiosus, herpes zoster, cervical erosin, decubital ulcer, hemorrhoid, inflammation of respiratory tract and the various types of dermatitis by use of this homocarnosine preparation.

Clinical Case No. 1

0.5% homocarnosine injection solution was administered to the wound brought about by a dental extraction.

TABLE 3

| | | | Dosage | Postoperative pains | | | Initial condition | | Conjoint |
|---|---|---|---|---|---|---|---|---|---|
| Case | Region | Diagnosis | (ml) | 2 hours | 12 hours | 24 hours | Edema | Cure | medicine |
| 1. Female, 28 yrs. | ⌐8 | Horizontal impaction | 0.3 | — | ± | — | — | ++ | None |
| 2. Male, 32 yrs. | 6⌐ | Alveolar osteitis | 0.3 | — | — | — | — | ++ | None |
| 3. Male, 20 yrs. | ⌐1 | Traumatic bone fracture | 0.1 | — | — | — | — | ++ | None |
| 4. Female, 43 yrs. | 4⌐ | Dental root cyst | 0.2 | — | + | — | — | ++ | None |
| 5. Female, 38 yrs. | 7⌐ | Alveolar osteitis | 0.3 | — | — | — | — | ++ | None |

Assessment criteria:
Pains:
— No subjective pains.
± Though subjective pains were present, no analgesic was used.
+ Subjective pains and an analgesic was administered.
Wound Healing:
++ Found to be highly effective compared with ordinary therapy.
+ Effective
— Non-effective Clinical Case No. 2

Patients who complained of the aftha stomatitis were injected with 0.5% homocarnosine solution.

TABLE 4

| Case | Region | Diagnosis | Dosage (ml) | Pains | Effect | Conjoint medicine |
|---|---|---|---|---|---|---|
| 1. Male, 18 yrs. | Gingivo-buccal junction of ⌐3 | Isolative aphtha | 0.1 | — | ++ | None |
| 2. Female, 36 yrs. | Tip of the tongue | Same | 0.1 | — | ++ | None |
| 3. Female, 38 yrs. | Lower surface of the tongue | Same | 0.1 | — | ++ | None |

Assessment Criteria

The patients in whom the pain disappeared immediately after injection of homocarnosine solution with no subsequent pain complaints on the following day, and the ulcerated area had shrunk postoperatively were assessed as favorable ++.

Clinical Case No. 3

0.5% homocarnosine in the form of a paste was applied in cases of angulus infectiosus in a dosage of 0.8 g on the basis of three times daily.

TABLE 5

| Case | Region | Diagnosis | Dosage (g) | Pains | Effect | Conjoint medicine |
|---|---|---|---|---|---|---|
| 1. Female, 29 yrs. | Right | Angulus infectiosus | 0.8 × 3 | — | ++ | None |
| 2. Female, 26 yrs. | Right and left | Same | 0.8 × 6 | — | + | None |
| 3. Male, 39 yrs. | Left | Same | 0.8 × 3 | — | ++ | None |
| 4. Female, 43 yrs. | Right and left | Same | 0.8 × 6 | — | + | None |

TABLE 5-continued

| Case | Region | Diagnosis | Dosage (g) | Pains | Effect | Conjoint medicine |
|---|---|---|---|---|---|---|
| 5. Female, 33 yrs. | Right | Same | 0.8 × 3 | — | ++ | None |
| 6. Male, 36 yrs. | Right | Same | 0.8 × 3 | — | ++ | None |

Assessment Criteria

In assessing the effect of treatment, those cases in which the wounds became closed on the day following homocarnosine administration were judged as ++ and those in which three applications were further needed before favorable results were obvious were judged as +.

Clinical Case No. 4

5% homocarnosine paste was applied to a case of herpes zoster.
Patient: Female, 63 yrs.
Region: The herpes zoster extended from the lower part of right breast to the side of body.
Course of the complaint: The patient came for consultation after three days of subjective complaint. 1 g of 5% homocarnosine paste was applied to the diseased region. In about one hour the pains disappeared completely with no relapse of the symptom. The same amount was applied five times daily (1 g/one time) and the cysts were rendered to be discolored and dry and the herpes symptom was assessed as having been cured after seven days.

Clinical Case No. 5

1.7 g suppository, one suppository containing 20 mg homocarnosine, was used for the following patients suffering from cervical erosion.

TABLE 6

| Case | Chief complaint | Diagnosis | Dosage | Effect |
|---|---|---|---|---|
| 1. 40 yrs. | Leukorrhea from 2 years earlier | Cervical erosion C II | 2 tablets in one day | Cured ++ |
| 2. 38 yrs. | Contact bleeding and leukorrhea from 3 years earlier | Cervical erosion C III$_a$ | 1 tablet daily for 7 days | Cured ++ |
| 3. 48 yrs. | Contact bleeding and leukorrhea from 2 years earlier | Cervical erosion C III$_b$ | 2 tablets daily for 7 days | Cured ++ |
| 4. 51 yrs. | Contact bleeding and leukorrhea | Cervical erosion C III$_c$ | 2 tablets daily for 14 days | Cured ++ |

Note:
1. The expression of cytologic findings is in accordance with the following classification.
Class I: Absence of atypical or abnormal cells
Class II: Atypical cytology but no evidence of malignancy
Class III: Cytologic suggestive of, but not conclusive for malignancy (Class III is further divided into Class III$_a$, Class III$_b$ and Class III$_c$. Class III$_a$ is close to benignancy and Class III$_c$ is close to malignancy. Class III$_b$ is in the middle.)
2. All the clinical cases cited above were confirmed as being non-malignant as the result of biopsy.
3. In evaluating the effect of homocarnosine the following criteria were adopted.
— Cases in which no improvement occured.
+ Cases in which there were no leukorrhea and contact bleeding in the eroded part of the vaginal cervox, the entire region being restored to the normal state.
++ Cases in which macroscopic inspection and pathohistodiagnosis confirmed the patient to be completely cured of Class I in terms of cytologic findings. There was no leukorrhea or contact bleeding and the degree of vaginal cleanliness was found normal with no other complications.

Clinical Case No. 6

1% homocarnosine ointment was applied to the cases of decubital ulcer as follows.

TABLE 7

| Case | Region (Length × width) | Period from outbreak of the disease | Dosage | Effect |
|---|---|---|---|---|
| 1. Male, 45 yrs. | Back (2 × 4 cm) | 6 months | 0.5–1.0 g once daily for 4 days | ++ |
| 2. Male, 30 yrs. | Nates (2 × 3 cm) | 3 months | 0.5–1.0 g once daily for 8 days | ++ |

Assessment criteria

— Non effective
+ Effective
++ Remarkably effective.

Clinical Case No. 7

1.7 g suppository, one suppository containing 10 mg homocarnosine, was used for the following patients suffering from hemorrohoid.

TABLE 8

| Case | Chief complaint | Diagnosis | Dosage | Effect |
|---|---|---|---|---|
| 1. Male, 29 yrs. | Pains and bleeding at defecation from 1 year earlier | Ractal bleeding | 1 tablet daily* for 4 days | ++ |
| 2. Male, 40 yrs. | Pains and bleeding at defecation from 3 years earlier | Inner hemorrhoids | 1 tablet daily for 14 days | ++ |

*Conjointly administered with 0.5% homocarnosine ointment.

Assessment criteria

— Non effective
+ Effective
++ Remarkably effective.

Clinical Case No. 8

0.1% homocarnosine solution in physiological saline was used for the following patients suffering from inflammation of respiratory tract with the aid of nebulizer.

TABLE 9

| Case | Diagnosis | Medication by a nebulizer | Effect |
|---|---|---|---|
| 1. Female, 23 yrs. | Allergic rhinitis | 0.8 ml × 2 | ++ |
| 2. Female, 41 yrs. | Inflamed respiratory tract | 1.0 ml × 1 | ++ |
| 3. Male, 32 yrs. | Inflamed respiratory tract | 1.0 ml × 3 | ++ |
| 4. Female, 28 yrs. | Tonsillitis | 1.0 ml × 3 | ++ |

TABLE 9-continued

| Case | Diagnosis | Medication by a nebulizer | Effect |
| --- | --- | --- | --- |
| 5. Male, 25 yrs. | Asthma | 1.0 ml twice daily for 10 days | ++ |

Assessment criteria

− Non effective
+ Effective
++ Remarkably effective.

Clinical Case No. 9

0.5% homocarnosine in the form of an ointment was applied to the following patients suffering from various types of dermatitis.

TABLE 10

| Case | Diagnosis | Dosage | Effect |
| --- | --- | --- | --- |
| 1. Female, 27 yrs. | Allergic dermatitis | 1.0 g twice daily | ++ |
| 2. Male, 70 yrs. | Geriatric itchiness | 0.5 g was applied before sleeping. A partial ulcer recovery was noted after one application | ++ |
| 3. Male, 41 yrs. | Eczema | 1.0 g twice daily for 2 days | ++ |
| 4. Male 25 yrs. | Burn (back of left hand) | 1.0 g was applied on the back of left hand once daily for 4 days | ++ |

Assessment criteria

− Non effective
+ Effective
++ Remarkably effective.

What is claimed is:

1. A method of treating inflammatory disease selected from the group consisting of wounds of all sorts, dental extraction wounds, aphtha ulcer, angulus infectiosus allergic rhinitis, tonsillitis, inflammation of respiratory tract, burn, herpes zoster, decubital ulcer, eczema, allergic dermatitis, geriatic itchness, stomach ulcer, ulcer of the duodenum, ulcers of the small and large intestines and the rectum, hemorrhoid, ulcer of the anus, cervical erosion, vaginal ulcer, ulcer of the outer genitalia, herpes and asthma in a human suffering therefrom comprising administering a preparation comprising homocarnosine or a physiologically acceptable salt thereof in an effective amount for treating the inflammatory disease in said human.

2. The method of treating inflammatory disease according to claim 1, wherein said preparation is administered in the form of an injection solution.

3. The method of treating inflammatory disease according to claim 1, wherein said preparation is administered in the form of granules.

4. The method of treating inflammatory disease according to claim 1, wherein said preparation is administered in the form of an ointment.

5. The method of treating inflammatory disease according to claim 1, wherein said preparation is administered in the form of a suppository.